United States Patent
Álvarez Micó et al.

(10) Patent No.: US 11,234,941 B2
(45) Date of Patent: Feb. 1, 2022

(54) OIL-FREE CAROTENOID COMPOSITION

(71) Applicant: GAT Therapeutics S.L., Barcelona (ES)

(72) Inventors: Xavier Álvarez Micó, Tarrasa-Barcelona (ES); Eugenia Ruiz Canovas, Granollers-Barcelona (ES); Ariadna Emeric Casterà, Barcelona (ES); Jaume Mercadé Roca, Barcelona (ES); Olga Durany Turk, Barcelona (ES); Jordi Segura De Yebra, Barcelona (ES)

(73) Assignee: GAT Therapeutics S.L., Barcelona (ES)

( * ) Notice: Subject to any disclaimer, the term of this patent is extended or adjusted under 35 U.S.C. 154(b) by 90 days.

(21) Appl. No.: 16/493,642

(22) PCT Filed: Mar. 14, 2018

(86) PCT No.: PCT/EP2018/056455
§ 371 (c)(1),
(2) Date: Sep. 12, 2019

(87) PCT Pub. No.: WO2018/167179
PCT Pub. Date: Sep. 20, 2018

(65) Prior Publication Data
US 2020/0000736 A1    Jan. 2, 2020

(30) Foreign Application Priority Data
Mar. 15, 2017 (EP) .................................... 17382133

(51) Int. Cl.
| | | |
|---|---|---|
| A61K 9/51 | (2006.01) | |
| A61K 31/12 | (2006.01) | |
| A61K 31/336 | (2006.01) | |
| B82Y 5/00 | (2011.01) | |

(52) U.S. Cl.
CPC .......... *A61K 9/5169* (2013.01); *A61K 9/5192* (2013.01); *A61K 31/12* (2013.01); *A61K 31/336* (2013.01); *B82Y 5/00* (2013.01)

(58) Field of Classification Search
CPC .......... A61K 9/51; A61K 21/336; A61K 31/12
IPC .................................................... A61K 9/5169
See application file for complete search history.

(56) References Cited

U.S. PATENT DOCUMENTS

2003/0175364 A1 * 9/2003 Newman ................ A61K 8/645
424/725

FOREIGN PATENT DOCUMENTS

| JP | 2008-110926 | 5/2008 |
| WO | 2003/066021 | 8/2003 |

OTHER PUBLICATIONS

Hashimoto et al., "The distribution and accumulation of fucoxanthin and its metabolites after oral administration in mice." British Journal of Nutrition Jan. 2009; vol. 102 issue 2. (Year: 2009).*
Bharathiraja, S. et al., "Astaxanthin conjugated polypyrrole nanoparticles as a multimodal agent for photo-based therapy and imaging", International Journal of Pharmaceutics, vol. 517, 2017, pp. 216-225.
Elzoghby, A.O. et al., "Albumin-based nanoparticles as potential controlled release drug delivery systems", Journal of Controlled Release, vol. 157, 2012, pp. 168-182.
Háda, M. et al., "Hydrophilic Carotenoids: Recent Progress", Molecules, vol. 17, 2012, pp. 5003-5012.
Santos, D.T. et al., "Production of stabilized sub-micrometric particles of carotenoids using supercritical fluid extraction of emulsions", The Journal of Supercritical Fluids, vol. 61, 2012 pp. 167-174.
Wackerbarth, H. et al., "Carotenoid-protein interaction as an approach for the formulation of functional food emulsions", Food Research International, vol. 42, 2009, pp. 1254-1258.
Wang, G. et al., "Preparation of BMP-2 Containing Bovine Serum Albumin (BSA) Nanoparticles Stabilized by Polymer Coating", Pharmaceutical Research, vol. 25, No. 12, 2008, pp. 2896-2909.
Zhu, J. e al., "Formation of nanocomplexes compromising whey proteins and fucoxanthin: Characterization, spectroscopic analysis, and molecular docking", Food Hydrocolloids, vol. 63, 2017, pp. 391-403.
International Search Report issued by the International Searching Authority (ISA/O.E.P.M.) dated May 18, 2018 in connection with International Application No. PCT/EP2018/056455.
Written Opinion of the International Searching Authority dated May 18, 2018 in connection with International Application No. PCT/EP2018/056455.

* cited by examiner

*Primary Examiner* — Walter E Webb
(74) *Attorney, Agent, or Firm* — Gary J. Gershik; Amster Rothstein & Ebenstein LLP (57) ABSTRACT

The invention relates to nanoparticles comprising a solid matrix, wherein the solid matrix comprises albumin and certain xanthophylls, and wherein the xanthophyll is distributed throughout the solid matrix. The present invention also relates to the method for obtaining the nanoparticles and to the products and compositions incorporating them.

16 Claims, 6 Drawing Sheets

OIL-FREE CAROTENOID COMPOSITION

CROSS-REFERENCE TO RELATED APPLICATIONS

This application is a § 371 national stage of PCT International Application No. PCT/EP2018/056455, filed Mar. 14, 2018, claiming priority of European Patent Application No. EP17382133.1, filed Mar. 15, 2017 the contents of each of which are hereby incorporated by reference into the application.

FIELD OF THE INVENTION

The present invention is comprised in the scope of food, nutraceutical, cosmeceutical and pharmaceutical technology. Particularly, it relates to nanoparticles comprising a matrix of albumin entrapping a xanthophyll or a derivative thereof, to a method for obtaining the nanoparticles and to their applications.

BACKGROUND OF THE INVENTION

Xanthophylls are a group of carotenoids containing an oxygen atom in their structure. Carotenoids are widely known naturally-occurring organic pigments. In addition to their colorant properties, these compounds have also been used as nutraceuticals and they also have shown important biological activity associated with antioxidant properties, such as strengthening the immune system, decreasing the risk of degenerative illnesses, reducing the risk of cardiovascular diseases, and preventing macular degeneration and cataracts. These antioxidant properties are mainly due to their capacity to act as potent direct oxygen radical scavengers and singlet oxygen quenchers.

Despite all these benefits, carotenoids are substantially hydrophobic and, therefore, they have a very low stability and solubility in water. Hydrophobicity in this context is rather a disadvantage because their use in medicine as antioxidants or in food chemistry as colorants would require water dispersability for their effective uptake. In fact, current administration of carotenoids is based on oily compositions mainly intended to be used orally which highly limits their absorption.

In this sense, organic solvents like dichloromethane of tetrahydrofuran are used to dissolve carotenoids at room temperature in oil. However, the latter is irritant to eyes and the respiratory system, and the toxicity of chlorohydrocarbons has evidenced a carcinogenic effect. Thus, the application of such organic solvents is therefore at least undesired in food production and for pharmaceutical applications.

In view of that, some attempts have been made to overcome this drawback or to obtain carotenoids with a certain degree of hydrophilicity.

One of these is based on the synthesis of carotenoid derivatives which are partially hydrophilic. This includes the preparation of hydrophilic salts of carotenoid esters, the complexation with cyclodextrins or the synthesis of PEGylated carotenoids (*Molecules*, 2012, 17, 5003-5012).

Other approach has been the formulation of carotenoids in oil-in-water emulsions for which a carotenoid-protein is previously formed and then mixed with a neutral oil, such as Mygliol (*Food Research International*, 2009, 42, 1254-1258).

Another alternative is to formulate carotenoids as a suspension of sub-micron particles and protecting the carotenoid with an encapsulation agent in order to reduce the degradation rate in aqueous media. This method also consists of producing an organic-in-water emulsion and dissolving the carotenoid in the organic phase of the emulsion. The organic solvent is then removed by evaporation. However, the production of gas bubbles during the evaporation of the solvent can disrupt the structure of the emulsion, resulting in low encapsulation efficiencies.

Another related technology to produce nanometer particles of carotenoids in aqueous media is the use of supercritical fluids in combination with nano-emulsions. This consists of extracting the organic solvent from the droplets of an oil-in-water emulsion with supercritical carbon dioxide (*The Journal of Supercritical Fluids*, 2012, 61, 167-174).

On the other hand, albumin is a water soluble and natural protein which has been used to prepare nanoparticles for drug delivery due to its biocompatible, biodegradable, non-toxic and non-immunogenic properties. Albumin nanoparticles have gained a considerable attention due to their high binding capacity of various drugs and for being well tolerated without any serious side-effects (*Journal of Controlled Release*, 2012, 157, 168-182).

In the last years, a great variety of physico-chemical processes for the preparation of albumin nanoparticles have been proposed, including thermal gelation, emulsification and desolvation (coacervation). In any case, the desolvation based-procedures appear to be the most popular due to their simplicity and repeatability. However, the just obtained nanoparticles are unstable and a supplementary step of physical, chemical or enzymatic stabilization has to be performed in order to prolong their half-life in aqueous environment and/or prevent from the formation of macro-aggregates of the protein.

In general, cross-linkage of the albumin is one of the most popular strategies for the stabilization of albumin nanoparticles, however the use of cross-linkers, such as glutaraldehyde, is questionable mainly due to its toxicity which hampers its use for in vivo delivery.

Surface coating has also been used to stabilize albumin nanoparticles. For example, cationic polymers, such as polylysine or polyethyleneimine, have been used to coat bovine serum albumin nanoparticles to improve their stability [Wang et al., *Pharm. Res.*, 2008, 25(12), 2896-2909].

Despite the different technologies developed in the prior art, an effective way to formulate carotenoids, particularly xanthophylls, in a free-oily composition which renders said compounds more stable in aqueous solution needs to be developed.

SUMMARY OF THE INVENTION

The authors of the present invention have found that a complex formed by the interaction of albumin with certain xanthophylls provides nanoparticles characterized for having a high stability in aqueous solution and, surprisingly, said nanoparticles do not need to be cross-linked or stabilized by other means, thus allowing the maintenance of its structure as well as of the biological activity of the carotenoid they incorporate. The complex formation is based on local hydrophobic interactions between albumin and xanthophyll.

The formulation of certain xanthophylls in the form of nanoparticles protects said compounds from being degraded in aqueous media, thus conferring a promising option to overcome the limitations of their very low stability and solubility in water and also to facilitate the incorporation of said compounds in compositions directed to different applications.

Actually, said nanoparticles of albumin and xanthophylls can be incorporated in foods as well as in cosmetic and pharmaceutical compositions and, therefore, they constitute a suitable carrier for the in vivo administration of carotenoids, either for nutraceutical, cosmetic and pharmaceutical applications.

The nanoparticles of the invention thus provide a new system for stabilizing certain xanthopylls. According to the present invention, a solid matrix of albumin is used as a vehicle for protecting the xanthophyll from the environmental conditions during long storage periods, thus increasing the lifetime and facilitating its administration in the human body.

Said nanoparticles may be used as a drug delivery system, enabling penetration and release or xanthophylls into targeted cells or organelles within the cell.

The nanoparticles have the additional advantage of being prepared in a simple manner, particularly, by means of a desolvation method which is applicable at industrial scale. Furthermore, this process allows nanoparticles to be spontaneously formed in the medium in which they are obtained by means of local interactions of the different components thereof, thus leading to a uniform dispersion of nanoparticles having a matrix-type structure wherein the xantho-phyll is distributed.

Therefore, a first aspect of the present invention relates to a nanoparticle comprising a solid matrix, said solid matrix comprising albumin and a xanthophyll selected from the group consisting of α-cryptoxanthin, β-cryptoxanthin, adonirubin, adonixanthin, alloxanthin, amarouciaxanthin A, antheraxanthin, auroxanthin, caloxanthin, cantaxanthin, capsanthin, capsanthin-5-6-epoxide, capsorubin, crocoxanthin, diadinoxanthin, diatoxanthin, echinenone, fucoxanthin, fucoxanthinol, iso-fucoxanthin, iso-fucoxanthinol, lutein, luteoxanthin, mutatoxanthin, neoxanthin, nostoxanthin, violaxanthin, zeaxanthin and combinations or derivatives thereof, wherein the weight ratio of albumin to xanthophyll ranges from 1:1 to 20:1.

In another aspect, the present invention refers to a method for obtaining the nanoparticles as defined above, said method comprises:
preparing an aqueous solution of albumin;
preparing a solution of a xanthophyll or a derivative thereof in an organic solvent;
adding the xanthophyll solution to the albumin solution, wherein the content of the organic solvent does not exceeds 20% v/v with respect to the total volume of the resulting mixture.

Another aspect of the invention relates to a composition comprising the nanoparticles provided by this invention. In a particular embodiment, said composition is free of any oily compound.

In another aspect, the invention relates to a food, nutraceutical, cosmeceutical or pharmaceutical product comprising i) the nanoparticle provided by this invention or ii) a composition provided by this invention.

A further aspect of the invention refers to a nanoparticle or a composition as defined above for use in the treatment or prevention of a disease involving the production of reactive oxygen species.

Another aspect of the invention refers to a nanoparticle or a composition as defined above for use in the treatment or prevention of a disease mediated by glucocorticoid receptor activity. Another aspect of the invention refers to the use of a nanoparticle or a composition as defined above, in the manufacture of a medicament for the treatment or prevention of a disease involving the production of reactive oxygen species.

Another aspect of the invention refers to the use of a nanoparticle or a composition as defined above, in the manufacture of a medicament for the treatment or prevention of a disease mediated by glucocorticoid receptor activity.

Another aspect of the invention refers to a method for the treatment or prevention of a disease involving the production of reactive oxygen specie comprising administering to a subject in need thereof a nanoparticle or a composition as defined above.

Another aspect of the invention refers to a method for the treatment or prevention of a disease mediated by glucocorticoid receptor activity comprising administering to a subject in need thereof a nanoparticle or a composition as defined above.

DETAILED DESCRIPTION OF THE INVENTION

For the purpose of facilitating the comprehension of the present invention, the meaning of some terms and expressions as used in the context of the invention are set forth below.

As used herein, the term "nanoparticle" refers to a colloidal system having spherical or quasi-spherical shape and having a mean size less than 1 µm, preferably in the range from 10 to 900 nanometers (nm). In a particular embodiment, the nanoparticle has a mean size ranging from 10 to 500 nm, more preferably from 10 to 200 or from 50 to 300 nm, even more preferably from 100 to 200 nm.

"Mean size" is understood as the average diameter of the nanoparticle population, moving together in an aqueous medium. The mean size of these systems can be measured by standard methods known by the person skilled in the art and are described, by way of illustration, in the experimental part below.

In the context of the present invention, the term nanoparticle can include a nanosphere and a nanocapsule.

By "nanosphere" should be understood a solid matrix of albumin or a continuous material of albumin wherein the xanthophyll is distributed throughout said matrix, thus not featuring a distinct core/shell structure. The local interactions between albumin and xanthophyll give rise to an organized structure or pattern wherein albumin forms a solid matrix which entraps the xanthophyll.

By "nanocapsule" should be understood a core/shell structure wherein the core is a solid matrix of albumin or a continuous material of albumin wherein the xanthophyll is distributed throughout said matrix, and the shell is a polymeric coating covering said matrix core.

Thus, in the scope of the present invention, nanoparticles are forming solid matrix systems. The solid matrix core of the nanoparticles of the invention has not differentiated external and internal structures and, therefore, the xanthophyll remains distributed within the entire matrix of albumin but not encapsulated or confined within a central cavity thereof.

In a particular embodiment, the nanoparticle is devoid of any polymeric coating, and therefore, the nanoparticle is a nanosphere as defined above. Thus, said nanoparticles comprise the solid matrix as described above and the xanthophyll and no coating layer/material coats or encases the solid matrix.

In a more particular embodiment, the nanoparticles of the invention consist of a solid matrix, said solid matrix comprising albumin and the xanthophyll or a derivative thereof, preferably a xanthophyll.

In another particular embodiment, the nanoparticle comprises a polymeric coating covering the solid matrix core, and therefore, the nanoparticle is a nanocapsule as defined above.

In another particular embodiment, the nanoparticles of the invention are characterized for having a solid core comprising a non-crosslinked matrix of albumin and xanthophyll, i.e., the matrix is solely formed by the local interactions between the albumin and the xanthophyll and no cross-linking agent is used to facilitate the formation of the matrix.

As used herein, the term "albumin" refers to a family of globular negatively charged proteins, the most common of which are the serum albumins. All the proteins of the albumin family are water-soluble, moderately soluble in concentrated salt solutions, and experience heat denaturation. Albumins are commonly found in blood plasma and differ from other blood proteins in that they are not glycosylated.

The general structure of albumin is characterized by several long α helices allowing it to maintain a relatively static shape, which is essential for regulating blood pressure.

In a particular embodiment, the albumin is a serum albumin. Serum albumin is produced in the liver and dissolved in blood plasma, being the most abundant protein in mammals.

More preferably, the serum albumin is human serum albumin (HSA) or bovine serum albumin (BSA), even more preferably the serum albumin is human serum albumin.

Human serum albumin is encoded by the ALB gene, whereas other mammalian forms, such as bovine serum albumin, are chemically similar.

Human serum albumin has a molecular weight of approximately 65.000 Da and consists of 585 amino acids. The amino acid sequence of HSA contains a total of 17 disulphide bridges, one free thiol (Cys34), and a single tryptophan (Trp214).

The term "carotenoid", as used herein, refers to a group of naturally-occurring pigments produced mainly by plants, yeast and microalgae, which have a common polyisoprenoid-based structure, a long polyene chain forming the chromophore and near symmetry around the central double bond. Tail-to tail linkage of two $C_{20}$ geranylgeranyl diphosphate molecules produces the parent $C_{40}$ carbon skeleton. The polyene chain may also have a cyclyl group at one or both ends of the molecule.

Figure 1:
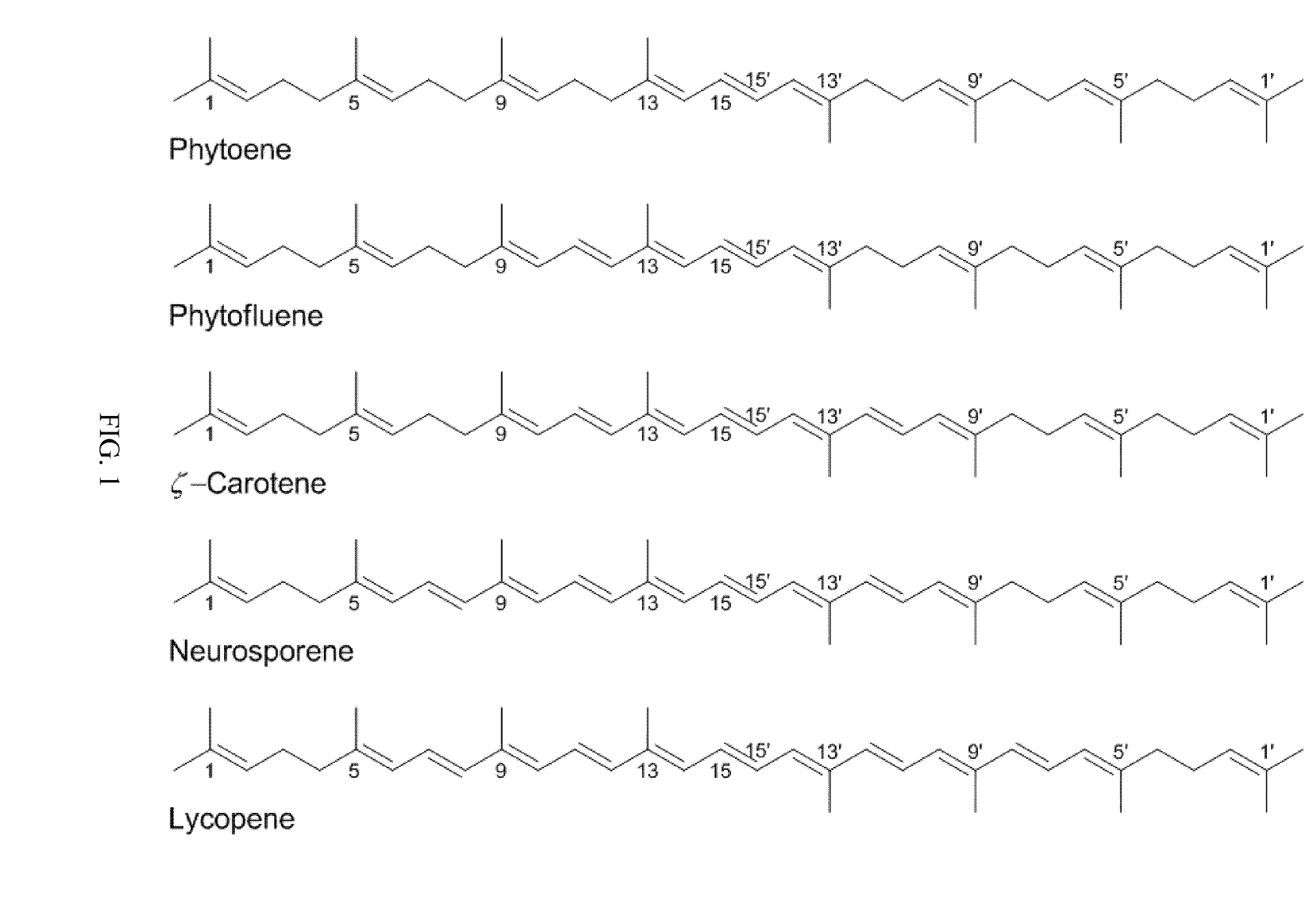
FIG. 1 shows the structure of carotenes phytoene, phytofluene, ζ-carotene, neurosporene, and lycopene.
Figure 2:
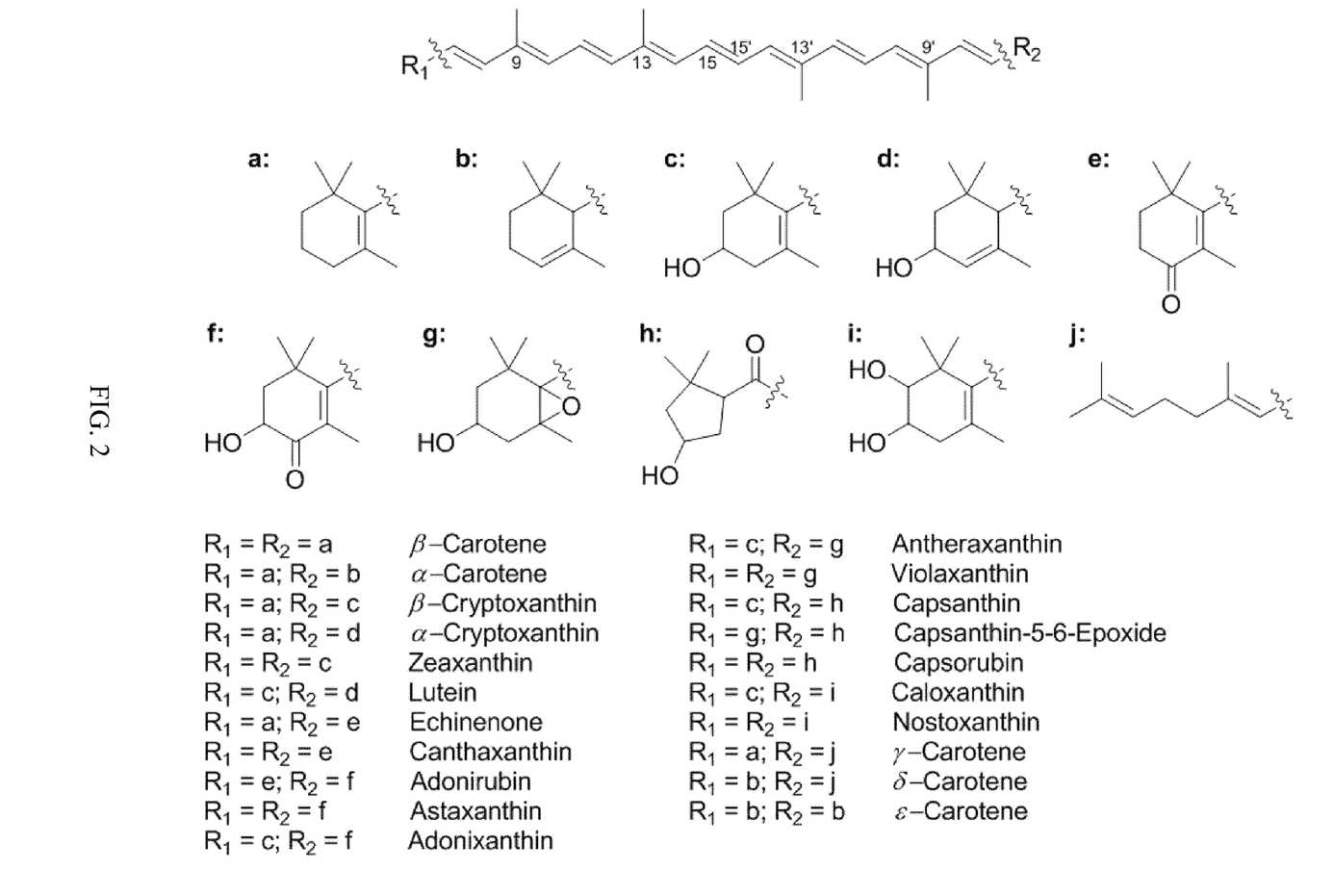
FIG. 2 shows the structure of xantophylls beta-cryptoxanthin, alpha-cryptoxanthin, zeaxanthin, lutein, echinenone, canthaxanthin, adonirubin, astaxanthin, adonixanthin, antheraxanthin, violaxanthin, capsanthin, capsanthin-5-6-epoxide, capsorubin, caloxanthin, and nostroxanthin, and of carotenes α-carotene, β-carotene, γ-carotene, δ-carotene and ε-carotene.
Figure 3:
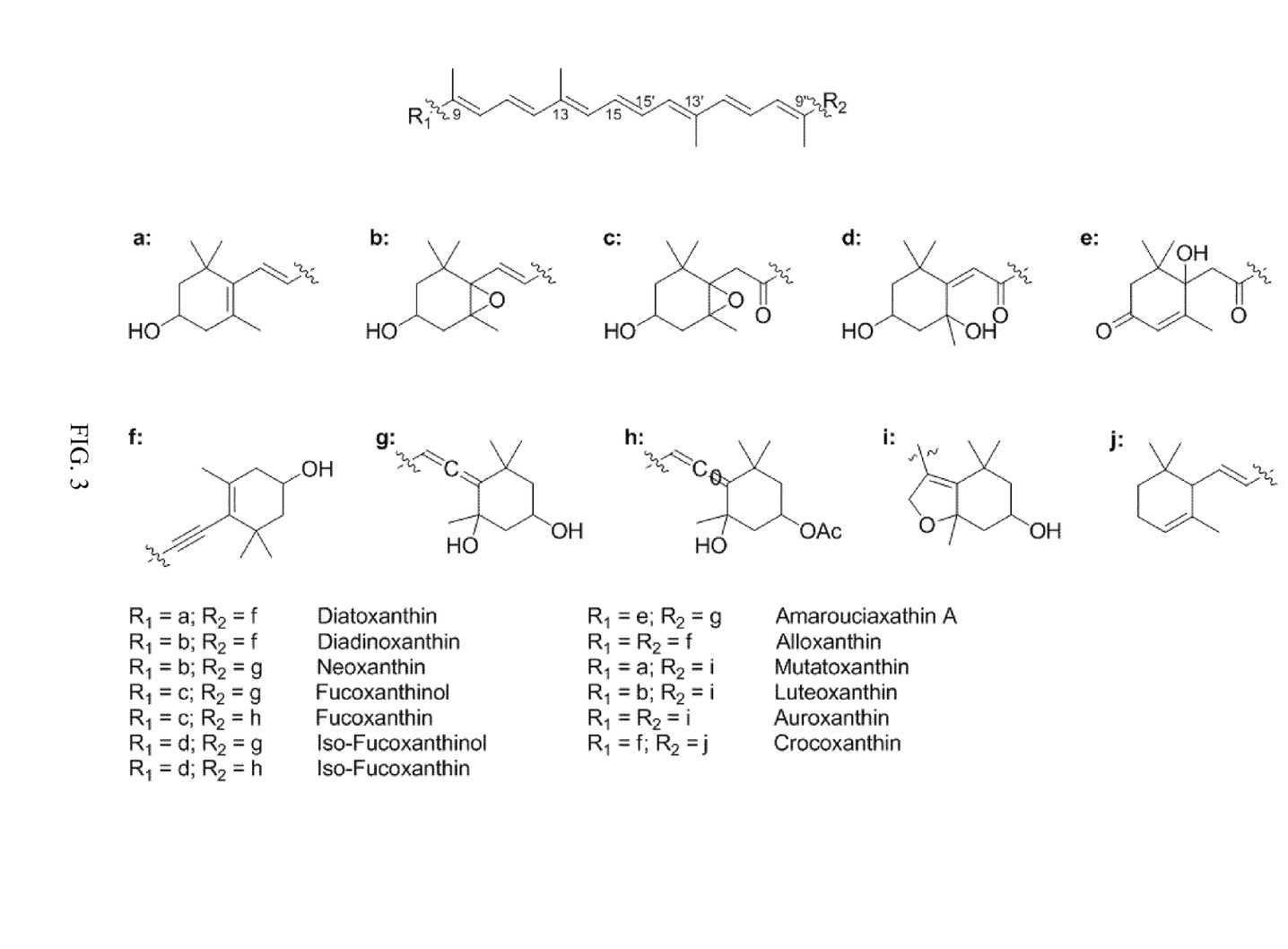
FIG. 3 shows the structure of xantophylls diatoxanthin, diadinoxanthin, neoxanthin, fucoxanthinol, fucoxanthin, iso-fucoxanthinol, iso-fucoxanthin, amarouciaxanthin A, alloxanthin, mutatoxanthin, luteoxanthin, auroxanthin and crocoxanthin.

Carotenoids are divided into two classes, xanthophylls (which contain oxygen atoms) and carotenes (which contain no oxygen atoms). Examples of carotenoids can be found in FIGS. 1, 2 and 3.

In the present invention, the xanthophyll is selected from the group consisting of α-cryptoxanthin, β-cryptoxanthin, adonirubin, adonixanthin, alloxanthin, amarouciaxanthin A, antheraxanthin, auroxanthin, caloxanthin, cantaxanthin, capsanthin, capsanthin-5-6-epoxide, capsorubin, crocoxanthin, diadinoxanthin, diatoxanthin, echinenone, fucoxanthin, fucoxanthinol, iso-fucoxanthin, iso-fucoxanthinol, lutein, luteoxanthin, mutatoxanthin, neoxanthin, nostoxanthin, violaxanthin, zeaxanthin and combinations or derivatives thereof. More preferably, the xanthophyll is selected from the group consisting of α-cryptoxanthin, β-cryptoxanthin, adonirubin, adonixanthin, alloxanthin, amarouciaxanthin A, antheraxanthin, auroxanthin, caloxanthin, cantaxanthin, capsanthin, capsanthin-5-6-epoxide, capsorubin, crocoxanthin, diadinoxanthin, diatoxanthin, echinenone, fucoxanthin, fucoxanthinol, iso-fucoxanthin, iso-fucoxanthinol, lutein, luteoxanthin, mutatoxanthin, neoxanthin, nostoxanthin, violaxanthin, zeaxanthin and combinations thereof. More preferably, the xanthophyll is selected from amarouciaxanthin A, fucoxanthin, fucoxanthinol, neoxanthin, lutein and combinations thereof. More preferably, the xanthophyll is selected from fucoxanthin, fucoxanthinol, neoxanthin, lutein and combinations thereof. Still more preferably, the xanthophyll is selected from amarouciaxanthin A, fucoxanthin, fucoxanthinol, neoxanthin and combinations thereof. Even more preferably the xanthophyll is fucoxanthin or neoxanthin.

In one embodiment, the xantophylles described above refer to the all-trans forms thereof.

The carotenoid, such as the above mentioned xanthophylls used in the nanoparticles of the invention, can be provided from an algal, fungal or plant extract.

When the carotenoid, such as the above mentioned xanthophylls used in the nanoparticles of the invention, comes from a plant extract, the product is obtained by an extractive process on any of the organisms or plants listed above, either by soaking said organisms or plants with a solvent or by extraction with more sophisticated techniques involving the use of pressure or supercritical fluids.

In the context of the present invention, the term "algal" or "algae" relates to both microalgae and macroalgae. Examples of suitable microalgae for the provision of carotenoids, such as the above mentioned xanthophylls used in the nanoparticles of the invention, include microalgae from the phylums Cyanophyta, Chlorophyta, Rhodophyta, Heterokontophyta, and Haptophyta. The algae from the phylum Cyanophyta can be Spirulina (Arthrospira), Aphanizomenon flos-aquae, Anabaena cylindrica or Lyngbya majuscule. The algae from the phylum Chlorophyta can be Chlorella, Scenedesmus, Dunaliella, Tetraselmis, Haematococcus, Ulva, Codium or *Caulerpa* spp. the algae from the phylum Rhodophyta can be *Porphyridium cruentum, Gracilaria* sp. *Grateloupia* sp, *Palmaria* sp. *Corallina* sp., *Chondrus crispus, Porphyra* sp. or *Rhodosorus* sp. The algae from the phylum Heterokontophyta can be Nannochlorropsis oculata, Odontella aurita, Phaeodactylum tricornutum. *Fucus* sp. *Sargassum* sp. *Padina* sp., *Undaria pinnatifida*, or *Laminaria* sp. The algae from the phylum Haptophyta can be *Isochrysis* sp. *Tisochrysis* sp. or *Pavlova* sp. The algae can be Chrypthecodinium cohnii, Schizochytrium, Ulkenia or Euglena gracilis. The algae can be a green microalga such as Chlorella, Scenedesmus, Dunaliella (for beta-carotene), Haematococcus (for astaxanthin) and Bracteacoccus; haptophyte microalgae such as Isochrysis (for fucoxanthin and lutein); and heterokontophyta microalgae such as Phaeodactylum, Ochromonas and Odontella. Examples of suitable macroalgae comprise all brown algae, and in particular Fucus vesiculosus, Fucus evanescens, *Laminaria* sp., and *Sargassum* sp. (all for fucoxanthin).

Certain fungi are known to produce xantophylls, such as Xanthophyllomyces dendrorhous. In addition, carotenoids can also be obtained from animal sources such as egg yolk.

Plants and plant parts suitable for the production of carotenoids, such as the xanthophylls used in the nanoparticles of the invention, include, without limitation, marigold flowers, maize, kiwi, red seedless grapes, zucchini, pumpkin, spinach, orange pepper, yellow squash, cucumber, pea, green pepper, red grape, butternut, orange, honeydew, celery, green grapes, Brussels sprouts, scallions, green beans, broccoli, apple, mango, green lettuce, tomato, peach, yellow pepper, nectarine, red pepper, carrots, cantaloupe, apricots, bell peppers and green kidney beans.

Derivatives of xanthophylls are also included in the context of the present invention. In a particular embodiment, said derivatives include xantophylles containing one or more cis double bond, including, without limitation, 9 cis derivatives, 9' cis derivatives, 13 cis derivatives, 13' cis derivatives, 15 cis derivatives, 15' cis derivatives and any combination thereof, wherein the numbering is as defined in FIGS. 1, 2 and 3.

In another embodiment, the xantophylles include synthetic derivatives thereof, wherein xantophylles are used as starting scaffolds for said derivatives. In some embodiments, the xanthophyll derivatives include compounds having a structure including a polyene chain (i.e., backbone of the molecule). Said polyene chain may include between about 5 and about 15 unsaturated bonds, more particularly 7 or more conjugated double bonds.

The albumin:xanthophyll weight ratio in the nanoparticles of the invention ranges from about 1:1 to about 20:1; more preferably from 2.5:1 to 20:1. A lower proportion of albumin would not provide a suitable matrix to entrap the xanthophyll, whereas a higher proportion of albumin would not render nanoparticles with enough activity for therapeutic purposes.

The nanoparticles of the invention have a particle size less than 1 μm, typically comprised between 10 and 900 nm, preferably between 10 and 500 nm, more preferably between 10 and 300 nm or from 50 to 300 nm, even more preferably between 10 and 200 nm or from 100 to 200 nm. This small size between 10 and 200 nm guarantees the nanoparticles to cross the cell membrane.

As mentioned above, and in a particular embodiment, the nanoparticle of the invention comprises a polymeric coating covering the solid matrix comprising the albumin and the xanthophyll or a derivative thereof, thus leading to a core/shell structure. The core is the solid matrix comprising the albumin and the xanthophyll or a derivative thereof and the shell is the polymeric coating.

By polymeric coating should be understood an external layer encapsulating the solid matrix. Said polymeric layer includes homopolymers, copolymers, such as for example, block, graft, random and alternating copolymers as well as terpolymers, further including their derivatives, combinations and mixtures thereof. These polymers should be biodegradable, i.e., they degrade during in vivo use, as well as biocompatible, i.e., substantially non-toxic or lacking injurious impact on the living tissues or living systems to which they come in contact with.

Biodegradable polymeric shells or coatings and method for their preparation are widely known in the art. In a particular embodiment, the polymeric coating comprises a material selected from a polylysine, polyethyleneimine, polylactide (PLA), poly(ε-caprolactone) (PLC), poly(glycolic acid) (PGA), poly(lactide-co-glycolide) (PLGA), chitosan, eudagrit, hyaluronic acid, alginate, carboxymethyl cellulose, carbopol, polyethylene glycol (PEG) poly(ethyl-2-cyanoacrylate) (PECA), polystyrene, poloxamers (such as Pluronic® block copolymers), hydroxypropyl methyl cellulose (HPMC), 2-hydroxyethyl methacrylate (HEMA), polyvinyl alcohol (PVA), poly(methyl acrylate) (PMA) and combinations thereof.

In another particular and optional embodiment, the nanoparticles of the invention further comprise a compound for protecting the matrix and the xanthophyll during the process of drying the nanoparticles, or of drying the suspension containing the nanoparticles of the invention by means of conventional methods, for example, by means of spray drying, hereinafter, "protecting agent". Said protecting agent does not form part of the solid matrix of the nanoparticles but acts as a bulking agent to facilitate the drying of nanoparticles in an efficient way, so as the structure thereof is maintained. Virtually, any compound complying with those characteristics can be used as a protecting agent. In a particular embodiment, said protecting agent is a saccharide.

Non-limiting, illustrative examples of protecting agents which can be used within the context of the present invention include lactose, mannitol, sucrose, maltodextrin, glucose, sorbitol, etc., as well as substances with prebiotic characteristics, such as for example, oligofructose, pectin, inulin, oligosaccharides (e.g. galacto-oligosaccharides, human milk oligosaccharides), lactulose, dietary fiber, etc., and any combination thereof. In a particular embodiment, the protecting agent is selected from maltodextrin, inulin, fructooligosaccharides and combinations thereof. If the nanoparticles of the invention include a protecting agent, the by weight ratio of the matrix and the protecting agent can vary within a wide range; nevertheless, in a particular embodiment, the albumin:protecting agent by weight ratio is 1:0.1-5, typically 1:0.5-4, preferably about 1:1.

Method for Obtaining the Nanoparticles of the Invention

Another aspect of the present invention refers to a process, hereinafter "process of the invention", for obtaining the nanoparticles as those described above.

Said process comprises:
a) preparing an aqueous solution of albumin;
b) preparing a solution of the xanthophyll or a derivative thereof in an organic solvent;
c) adding the xanthophyll solution to the albumin solution, wherein the content of the organic solvent does not exceeds 20% v/v with respect to the total volume of the resulting mixture.

This method is based on the coacervation process. Coacervation is a desolvation process wherein aqueous solutions of albumin are slowly desolvated by slow addition (such as dropwise addition) of a desolvating agent (typically an organic solvent such as ethanol, acetone or THF), under constant stirring, temperature and pH conditions.

More particularly, step a) of the process of the invention provides an aqueous solution of albumin. In a preferred embodiment, the albumin is human serum albumin or bovine serum albumin.

The solution of the albumin can be prepared by conventional methods known by those skilled in the art, for example by adding the albumin to the aqueous solution.

The amount of albumin that can be added to the aqueous solution can vary within a wide range, nevertheless, in a particular embodiment, the amount added to said aqueous solution is comprised between 0.1% and 15% (w/v), preferably between 0.2% and 10% (w/v), even more preferably between 0.2% and 5% (w/v).

In a preferred embodiment, the aqueous solution of the albumin is subjected to homogenization by means, for example, of stirring.

The process of the invention further comprises the preparation of a solution of the xanthophyll or a derivative thereof.

The xanthophyll is selected from the group consisting of α-cryptoxanthin, β-cryptoxanthin, adonirubin, adonixanthin, alloxanthin, amarouciaxanthin A, antheraxanthin, auroxanthin, caloxanthin, cantaxanthin, capsanthin, capsanthin-5-6-epoxide, capsorubin, crocoxanthin, diadinoxanthin, diatoxanthin, echinenone, fucoxanthin, fucoxanthinol, iso-fucoxanthin, iso-fucoxanthinol, lutein, luteoxanthin, mutatoxanthin, neoxanthin, nostoxanthin, violaxanthin, zeaxanthin and combinations or derivatives thereof. More preferably, the xanthophyll is selected from the group consisting of α-cryptoxanthin, β-cryptoxanthin, adonirubin, adonixanthin, alloxanthin, amarouciaxanthin A, antheraxanthin, auroxanthin, caloxanthin, cantaxanthin, capsanthin, capsanthin-5-6-epoxide, capsorubin, crocoxanthin, diadinoxanthin, diatoxanthin, echinenone, fucoxanthin, fucoxanthinol, iso-fucoxanthin, iso-fucoxanthinol, lutein, luteoxanthin, mutatoxanthin, neoxanthin, nostoxanthin, violaxanthin, zeaxanthin and combinations thereof. More preferably, the xanthophyll is selected from amarouciaxanthin A, fucoxanthin, fucoxanthinol, neoxanthin, lutein and combinations thereof. More preferably, the xanthophyll is selected from fucoxanthin, fucoxanthinol, neoxanthin, lutein and combinations thereof. Still more preferably, the xanthophyll is selected from amarouciaxanthin A, fucoxanthin, fucoxanthinol, neoxanthin and combinations thereof. Even more preferably the xanthophyll is fucoxanthin or neoxanthin.

The solution of the xanthophyll is prepared with an organic solvent. The election of said organic solvent depends on the solubility of the xanthophyll used to obtain the nanoparticles. However, in a preferred embodiment said organic solvent is selected from ethanol and tetrahydrofuran (THF).

The amount of xanthophyll which may be present in the organic solution can vary within a wide range; nevertheless, in a particular embodiment, the amount of xanthophyll present in the organic solution is comprised between 0.1 and 5% (w/v), preferably between 0.1% and 2% (w/v), even more preferably between 0.2% and 1% (w/v).

Once the aqueous solution of albumin and the organic solution of xanthophyll or a derivative thereof are prepared, the xanthophyll solution is slowly added to the albumin solution, preferably under stirring. More preferably, the xanthophyll solution is dropwise added to the aqueous solution of albumin while stirring the resulting mixture.

In a preferred embodiment, said addition is carried out under an inert atmosphere, such as under nitrogen atmosphere.

The albumin and the xanthophyll are preferably mixed at room temperature, i.e., at a temperature comprised between 18° C. and 25° C., preferably between 20° C. and 22° C.

In a particular embodiment, the albumin and the xanthophyll are added to their respective solutions so as the albumin:xanthophyll weight ratio ranges from 1:1 to 25:1; more preferably from 1:1 to 20:1, even more preferably from 2.5:1 to 20:1.

After mixing the albumin and xanthophyll under the aforementioned conditions, i.e., at room temperature and under stirring, the nanoparticles of the invention are spontaneously formed. In a particular embodiment, said nanoparticles are in suspension in the medium in which they have been obtained.

Thus, the process of the invention allows the formation of a uniform dispersion of nanoparticles by means of simple coacervation, leading to solid nanospheres having a matrix-type structure wherein the xanthophyll is distributed within the whole albumin matrix.

Therefore, the nanoparticles obtained by the process of the invention can be considered as self-assembling nanoparticles which are spontaneously formed by means of local interactions upon mixture of the xanthophyll solution with the aqueous albumin solution.

Thus, the present invention also refers to nanoparticles obtainable by the process of the present invention. More particularly, the invention refers to a nanoparticle suspension obtainable by the process as defined above.

In a particular embodiment, the nanoparticles already formed are incubated for at least 10 minutes.

In another particular embodiment, the process for producing a nanoparticle according to the invention comprises an additional step of removing the organic solvent used in step b) (for example, by means of evaporation under reduce pressure), and/or optionally purifying (for example, by means of filtration techniques, centrifugation or ultracentrifugation).

Likewise, if desired, said process of the invention may include an additional step of drying the formed nanoparticles in order to obtain the nanoparticles of the invention in the form of a powder. This form of presentation of said nanoparticles contributes to their stability and is further particularly useful for their eventual application in pharmaceutical products.

In a preferred embodiment, the suspension resulting from the mixture of albumin and the xanthophyll which contains the nanoparticles of the invention is subjected to a drying treatment by conventional methods, for example vacuum drying or, advantageously by means of spray drying or by means of lyophilization, in order to dry the nanoparticles of the invention.

In a particular embodiment, this drying treatment, particularly when it is performed by means of spray drying or by means of lyophilization, comprises adding a protecting agent to the nanoparticles of the invention once they are formed. This protecting agent protects the matrix and the xanthophyll during the drying process thereof, such as for example, a saccharide.

Non-limiting, illustrative examples of saccharides which can be used as protecting agents within the context of the present invention include lactose, mannitol, sucrose, maltodextrin, glucose, sorbitol, etc., as well as polysaccharides with prebiotic characteristics, such as for example, oligofructose, pectin, inulin, oligosaccharides (e.g. galacto-oligosaccharides, human milk oligosaccharides), lactulose, dietary fiber, etc. and mixtures thereof. In a particular embodiment, the protecting agent is selected from maltodextrin, inulin, fructooligosaccharides (FOS) and combinations thereof. If the nanoparticles of the invention include a protecting agent, this is added in the suitable amount; even though the by weight ratio of the matrix of nanoparticles and the protecting agent can vary within a wide range, in a particular embodiment, the albumin:protecting agent by weight ratio is 1:0.1-5, typically 1:0.5-4, preferably about 1:1.

In a particular embodiment in which the method of the invention comprises drying the suspension of nanoparticles of the invention, said suspension of nanoparticles of the invention are dried by means of spray drying. To that end, the suspension containing the nanoparticles of the invention and the protecting agent is introduced in a spray-dryer and the processing conditions [air inlet temperature, air outlet temperature, air pressure, sample pumping rate, suction, and airflow] are controlled. The person skilled in the art can set the processing conditions that are most suitable for each case.

The method of the invention allows obtaining the nanoparticles of the invention in the form of a dry powder, which contributes to the stability of the nanoparticles of the invention during long storage periods under controlled or environmental conditions and it can also be easily incorporated in different intended solid and liquid products.

Since the nanoparticles are formed previously to the addition of the protecting agent, this does not form any conjugate or complex with the albumin-xanthophyll matrix.

The nanoparticles obtainable after conducting said drying process thus constitute an additional aspect of the present invention. Accordingly, the invention also refers to nanoparticles obtainable by the process of the invention which includes the drying treatment mentioned above.

More particularly, the invention refers to a dry powder of nanoparticles obtainable by the process of the invention which includes the drying treatment mentioned above.

Applications

The nanoparticles of the invention have the capacity to entrap a xanthophyll and to protect them during processing and storage as well as until its final delivery to the biological site of interest. The degradation of the xanthophyll after incorporation in the different intended products (e.g., pharmaceutical compositions, cosmetic compositions or foods) is thus prevented or substantially reduced.

Therefore, in another aspect, the invention relates to a composition comprising the nanoparticles as defined above, or the nanoparticle obtainable by means of the method of the invention, either in the form of a suspension or in dry powder form.

In a particular embodiment, said composition is selected from:
(a) a composition consisting in a plurality of nanoparticles of the invention, or in a plurality of nanoparticles obtainable by means of the method of the invention; and
(b) a composition comprising a plurality of nanoparticles of the invention or a plurality of nanoparticles obtainable by means of the method of the invention, and a food, nutraceutical, cosmeceutical or pharmaceutical acceptable vehicle.

The characteristics of the nanoparticles of the invention have already been defined above and are incorporated herein by reference.

In a particular embodiment, the nanoparticles of the invention are in the form of a dry powder in the composition of the invention.

In the first case, the composition of the invention (a) is made up only and exclusively of nanoparticles of the invention and/or nanoparticles obtainable by means of the method of the invention.

In the second case, the composition of the invention (b) comprises the nanoparticles of the invention and/or the nanoparticles obtainable by means of the method of the invention, and a food, nutraceutical, cosmeceutical or pharmaceutical acceptable vehicle or carrier.

The person skilled in the art will understand that the nanoparticles of the invention or the compositions containing them can be part of a food or feed, or of a nutraceutical, pharmaceutical, or cosmeceutical product, which constitutes an additional aspect of the present invention.

Thus, a further aspect of the present invention relates to a food, pharmaceutical, cosmeceutical or nutraceutical product comprising i) the nanoparticles of the invention and/or the nanoparticles obtained by means of the method of the invention, or ii) a composition comprising the nanoparticles of the invention and/or one the nanoparticles obtainable by means of the method of the invention, whatever composition (a) or composition (b). Said product can be in a liquid, semi-solid or solid form.

In a particular embodiment, the product of the invention is a food or feed comprising i) the nanoparticles of the invention and/or the nanoparticles obtainable by means of the method of the invention, or ii) a composition comprising the nanoparticles of the invention and/or the nanoparticles obtainable by means of the method of the invention, and a food acceptable vehicle or carrier.

As used herein, the term "food" is any substance or product of any nature, solid or liquid, natural or processed which due to its characteristics, applications, components, preparation and state of preservation, can usually or ideally be used for some of the following purposes: a) as normal nutrition for human beings or animals or as pleasurable foods; or b) as dietetic products, in special cases of human or animal food. The term "feed" includes all the natural materials and finished products of any origin which, separately or conveniently mixed with one another, are suitable as animal food.

A ready-to-eat food is that which does not need to be diluted by means of an aqueous solution suitable for consumption for example. In principle, the ingredients present in a ready-to-eat food are balanced and there is no need to add additional ingredients to the food to make it ready to eat, such considered by a person skilled in the art. A concentrated food is that in which one or more ingredients are present at a higher concentration than in a ready-to-eat food, therefore for use it is necessary to dilute it by means of an aqueous solution suitable for consumption for example. Non-limiting, illustrative examples of foods provided by this invention include both dairy products and derivatives, for example, fermented milks, yoghurt, kephir, curd, cheeses, butters, ice creams, milk-based desserts, etc., and non-dairy products, such as baked products, cakes and pastries, cereals, chocolates, jams, juices, other fruit derivatives, oils and margarines, prepared dishes, etc.

In another particular embodiment, the product of the invention is a nutraceutical product comprising i) the nanoparticles of the invention and/or the nanoparticles obtainable by means of the method of the invention, or ii) a composition comprising the nanoparticles of the invention and/or the nanoparticles obtainable by means of the method of the invention, and a nutraceutical acceptable carrier.

As used herein, the term "nutraceutical product" refers to a product suitable for use in human beings or animals, comprising one or more natural products with therapeutic action which provide a health benefit or have been associated with disease prevention or reduction, and it includes dietary supplements presented in a non-food matrix (e.g., capsules, powder, etc.) of a concentrated natural bioactive product usually present (or not) in the foods and which, when taken in a dose higher than that existing in those foods, exerts a favorable effect on health which is greater than effect which the normal food may have. Therefore, the term "nutraceutical product" includes isolated or purified food products as well as additives or food supplements which are generally presented in dosage forms normally used orally, for example, capsules, tablets, sachets, drinkable phials, etc.; such products provide a physiological benefit or protection against diseases, generally against chronic diseases. If desired, the nutraceutical product provided by the invention can contain, in addition to the xanthophylls, one or more nutraceuticals (products or substances associated with disease prevention or reduction), for example, flavonoids, omega-3 fatty acids, etc., and/or one or more prebiotics (non-digestible food ingredients which stimulate probiotic activity and/or growth), for example, oligofructose, pectin, inulin, galacto-oligosaccharides, lactulose, human milk oligosaccharides, dietary fiber, etc.

In another particular embodiment, the product of the invention is a cosmeceutical product comprising i) the nanoparticles of the invention and/or the nanoparticles obtainable by means of the method of the invention, or ii) a composition comprising the nanoparticles of the invention and/or the nanoparticles obtainable by means of the method of the invention, and a cosmeceutical acceptable vehicle or carrier. As used herein, the term "cosmeceutical product" refers to a product suitable for use in the body or animal body comprising one or more cosmeceutical products (functional cosmetics, dermaceuticals or active cosmetics), i.e., topical hybrid products with cosmetic-pharmaceutical characteristics containing active ingredients having effect on user's skin, hair and/or nails, at higher and more effective concentrations, therefore they are located in an intermediate level between cosmetic and drug. Illustrative examples of cosmeceutical products include essential oils, ceramides, enzymes, minerals, peptides, vitamins, etc.

In another particular embodiment, the product of the invention is a pharmaceutical product comprising i) the nanoparticles of the invention and/or the nanoparticles obtainable by means of the method of the invention, or ii) a composition comprising the nanoparticles article of the invention and/or the nanoparticles obtainable by means of the method of the invention, and a vehicle or carrier suitable for oral, topical or parenteral administration. More preferably, the pharmaceutical product comprises a vehicle or carrier suitable for oral or parenteral administration.

Based on the particular mode of administration, the pharmaceutical product may be formulated into tablets, pills, capsules, sachets, granules, powders, suspensions, emulsions, anhydrous or hydrous topical formulations and solutions.

The pharmaceutical acceptable carriers or vehicles are well-known to those skilled in the art and are readily available to the public. It is preferred that the pharmaceutically acceptable carrier or vehicle be one which is chemically inert to the active formulation and each of its components and one which has no detrimental side effects or toxicity under the conditions of use.

In some embodiments, the pharmaceutical product is adapted as a delivery system for transporting the therapeutic agent orally, parenterally or intravenously into the circulatory system of a subject.

Formulations suitable for oral administration include liquid solutions, such as an effective amount of the nanoparticles, or composition comprising the same, dissolved in diluents, such as water or saline; capsules, sachets, tablets, lozenges, each containing a predetermined amount of the nanoparticles; powders; suspensions in an appropriate liquid; and emulsions.

The parenteral formulations will typically contain from 0.5 to 25% by weight of the nanoparticles in solution. Said formulations can be presented in unit-dose or multi-dose sealed containers, such as ampules and vials, and can be stored in freeze-dried (lyophilized) conditions requiring only the addition of the sterile liquid carrier, for example, water for injections, immediately prior to use.

The administration of xanthophylls or a derivative thereof may inhibit and/or ameliorate the occurrence of diseases in subjects. Such diseases include those involving the production of reactive oxygen species and/or other radical and non-radical species (for example singlet oxygen, a reactive oxygen species but not a radical). In a first category are those disease conditions in which a single organ is primarily affected and for which evidence exists that radicals and/or non-radicals are involved in the pathology of the disease. In a second category are multiple-organ conditions whose pathology has been linked convincingly in some way to radical and non-radical injury.

Examples of disease conditions involving the production of reactive oxygen species are ischemia-reperfusion injury, a liver disease, age-related immune deficiency and premature aging disorders, age-related macular degeneration, retinal detachment, hypertensive retinal disease, uveitis, degenerative retinal damage, cataractogenesis, retinopathy, Meuniere's disease, drug-induced toxicity, infectious otitis, idiopathic otitis, infectious sinusitis, gastrointestinal diseases, musculoskeletal diseases, cardiovascular diseases, cerebrovascular diseases and cancer.

Thus, another aspect of the present invention relates to a nanoparticle or a composition as defined above which contains a xanthophyll selected from the group consisting of α-cryptoxanthin, β-cryptoxanthin, adonirubin, adonixanthin, alloxanthin, amarouciaxanthin A, antheraxanthin, auroxanthin, caloxanthin, cantaxanthin, capsanthin, capsanthin-5-6-epoxide, capsorubin, crocoxanthin, diadinoxanthin, diatoxanthin, echinenone, fucoxanthin, fucoxanthinol, iso-fucoxanthin, iso-fucoxanthinol, lutein, luteoxanthin, mutatoxanthin, neoxanthin, nostoxanthin, violaxanthin, zeaxanthin and combinations or derivatives thereof for use in the treatment or prevention of a disease involving the production of reactive oxygen species, such as those diseases mentioned above. In another aspect, the invention relates to the use of a nanoparticle or a composition as defined above in the manufacture of a medicament for the treatment or prevention of a disease involving the production of reactive oxygen species, such as those diseases mentioned above. In a further aspect, the invention relates to a method for the treatment or prevention of a disease involving the production of reactive oxygen species, such as those diseases mentioned above, comprising administering to a subject in need thereof a nanoparticle or a composition as defined above, preferably a therapeutically effective amount of said nanoparticle or composition.

The authors of the present invention have also identified that certain xanthophylls act as modulators of the glucocorticoid receptor. Therefore, in another aspect, the invention relates to a nanoparticle or a composition as defined above which contains a xanthophyll selected from the group consisting of α-cryptoxanthin, β-cryptoxanthin, adonirubin, adonixanthin, alloxanthin, amarouciaxanthin A, antheraxanthin, auroxanthin, caloxanthin, cantaxanthin, capsanthin, capsanthin-5-6-epoxide, capsorubin, crocoxanthin, diadinoxanthin, diatoxanthin, echinenone, fucoxanthin, fucoxanthinol, iso-fucoxanthin, iso-fucoxanthinol, lutein, luteoxanthin, mutatoxanthin, neoxanthin, nostoxanthin, violaxanthin, zeaxanthin and combinations or derivatives thereof for use in the treatment or prevention of a disease mediated by glucocorticoid receptor activity. In another aspect, the invention relates to the use of a nanoparticle or a composition as defined above in the manufacture of a medicament for the treatment or prevention of a disease mediated by glucocorticoid receptor activity. In a further aspect, the invention relates to a method for the treatment or prevention of a disease mediated by glucocorticoid receptor activity comprising administering to a subject in need thereof a nanoparticle or a composition as defined above, preferably a therapeutically effective amount of said nanoparticle or composition.

The term "glucocorticoid receptor", also known as GR, GCR, or NR3C1 (nuclear receptor subfamily 3, group C, member 1), as used herein refers to the receptor to which cortisol and other glucocorticoids bind. The human gene is shown in the Ensembl database under accession number ENSG00000113580.

As used herein, the terms "corticoids" or "corticosteroids" refer to a class of steroid hormones that are produced in the adrenal cortex of vertebrates, as well as the synthetic analogues of these hormones. Corticosteroids are involved in a wide range of physiological processes, including stress response, immune response, and regulation of inflammation, carbohydrate metabolism, protein catabolism, blood electrolyte levels, and behavior. There are two types of corticoids, glucocorticoids and mineralocorticoids.

Glucocorticoids are corticosteroids that bind to the glucocorticoid receptor. The structure of glucocorticoids comprises a steroid ring system.

As used herein, the term "cortisol" or "hydrocortisone" refers to a glucocorticoid of formula:

The term "treatment", as used herein, refers to any type of therapy, which is aimed at terminating, preventing, ameliorating or reducing the susceptibility to a clinical condition as described herein. In a preferred embodiment, the term treatment relates to prophylactic treatment (i.e. a therapy to reduce the susceptibility to a clinical condition), of a disorder or a condition as defined herein. Thus, "treatment," "treating," and their equivalent terms refer to obtaining a desired pharmacologic or physiologic effect, covering any treatment of a pathological condition or disorder in a mammal, including a human. The effect may be prophylactic in terms of completely or partially preventing a disorder or symptom thereof and/or may be therapeutic in terms of a partial or complete cure for a disorder and/or adverse effect attributable to the disorder. That is, "treatment" includes (1) preventing the disorder from occurring or recurring in a subject, (2) inhibiting the disorder, such as arresting its development, (3) stopping or terminating the disorder or, at least, symptoms associated therewith, so that the host no longer suffers from the disorder or its symptoms, such as causing regression of the disorder or its symptoms, for example, by restoring or repairing a lost, missing or defective function, or stimulating an inefficient process, or (4) relieving, alleviating, or ameliorating the disorder, or symptoms associated therewith, where ameliorating is used in a broad sense to refer to at least a reduction in the magnitude of a parameter, such as inflammation, pain, or immune deficiency.

In another embodiment of the invention the disease characterized by an undesired glucocorticoid activity is selected from the group consisting of cortisol-induced immunosuppression, cortisol-induced insulin resistance, altered skin barrier homeostasis, Cushing s syndrome, subclinical Cushing s syndrome, subclinical hypercortisolemia, metabolic syndrome, inflammatory bowel disease, muscle wasting and muscle dystrophy, insomnia associated to circadian rhythm disorders, hypertension, water retention, cortisol-induced DNA damage, migraine, psychosis, appetite reduction, depression, stress disorders and cognitive disorders such as Alzheimer's disease catatonia, amyotrophic lateral sclerosis, delirium, post-traumatic stress disorders, impaired memory retrieval, or borderline personality disorder.

The following examples illustrate the invention and must not be considered as limiting the same.

EXAMPLES

Example 1

Preparation of the Nanoparticles

For the preparation of these nanoparticles, human serum albumin (HAS) and bovine serum albumin (BSA) were used as matrix-forming materials. Fucoxanthin and neoxanthin were used as xanthophylls.

Nanoparticles having the following albumin:xanthophyll weight ratio were prepared: 20:1; 10:1; 5:1 and 2.5:1.

To prepare bovine serum albumin (BSA) or human serum albumin (HAS)—xanthophyll nanoparticles, albumin (20 mg, 10 mg, 5 mg or 2.5 mg depending on the protein: xanthophyll ratio) was dissolved in 1 mL deionized water and 1 mg of xanthophyll was dissolved in 0.25 mL ethanol or THF, depending on the relative solubility of each xanthophyll. The xanthophyll solution was slowly added to the protein solution under stirring and nitrogen atmosphere. The nanoparticles were incubated at room temperature for 10 additional minutes. The organic solvent (ethanol or THF) in the mixed solution was slowly removed by speed vacuum or rotary evaporation at 25° C. Distillation is completed when the total volume of the solution is reduced by ⅔. The solution can be stored stably a 4° C. and/or lyophilized by freeze drying.

Example 2

Measurement of Particle Size

Two independently prepared samples with the highest w/w ratio (BSA:fucoxanthin) of 20:1 were assessed for particle size distribution in aqueous solution by means of a dynamic light scattering measuring device (Möbζ apparatus, Wyatt Technologies). The following table summarizes the measurements performed:

|  | Average particle diameter (nm) | Polydispersity (nm) | Z' potential |
| --- | --- | --- | --- |
| Sample 1 | 140 | 16 | −340 |
| Sample 2 | 143 | 16 | −338 |

Example 3

Stability of Nanoparticles

This is aimed to determine the stability of xanthophyll in nanoparticles dispersed in aqueous solution.

The stability of the xanthophylls in the nanoparticles was assessed 7 and 14 days after preparation.

The analysis of the stability of the xanthophyll was performed by means of a 1100 series HPLC device (Agilent Technologies, Waldbronn, Germany) with a diode array detector (450 nm). Separations were performed on a 250× 4.6 mm Kromaphase C18 column (Bischoff, Leonberg, Germany) with an average pore diameter of 100 Å and a particle size of 5 μm at a temperature of 25° C. Separation was achieved using a mobile phase composition of acetone (A) and water (B) an at a flow rate of 1 mL/min. The elution proceeded isocratically at 80% A for 4 min, and was followed by a linear gradient to 100% A until 16 min. This percentage of A was maintained for 4 additional minutes. The injection volume was 5 μL.

For the analysis of stability of nanoparticles in solution, 50 μl samples of the solution were mixed with 450 μL of acetone and stirred for 30 min on an orbital shaker for 30 min. The solution was then centrifuged at 5000 rpm for 5 min. The supernatant was recovered by decantation and used for HPLC analysis. Freeze-dried samples were dissolved in deionized water prior to following the same preparation process than samples already in solution.

Figure 4:
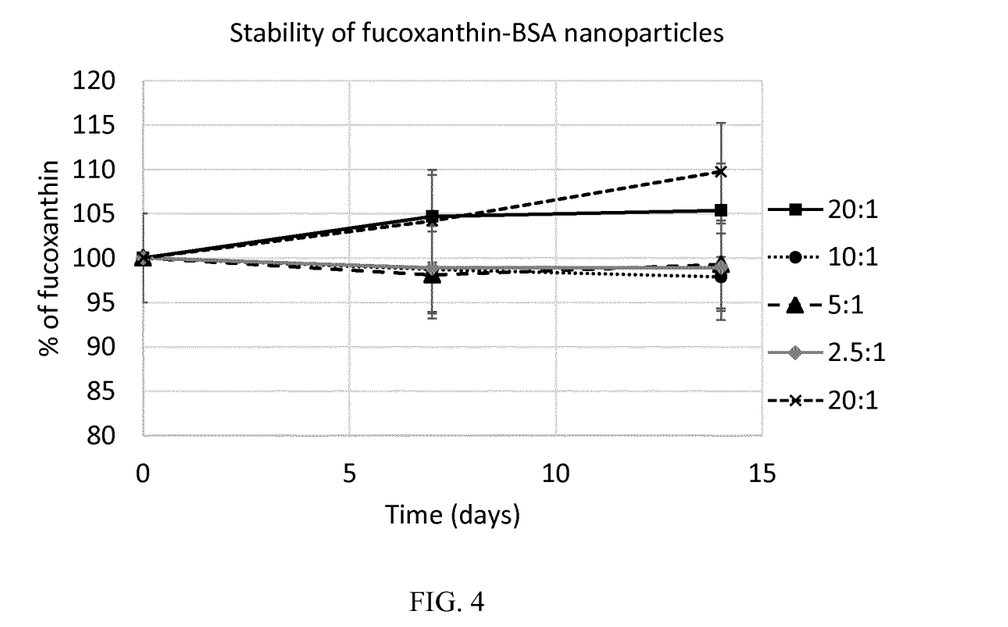
FIG. 4 shows the percentage of fucoxanthin in nanoparticles of bovine serum albumin (BSA) and fucoxanthin dispersed in aqueous solution after 7 and 14 days from their preparation. Weight ratio albumin/fucoxanthin (■) 20:1; (●) 10:1; (▲) 5:1; (◆) 2.5:1; (x) 20:1 lyophilized nanoparticles.
Figure 5:
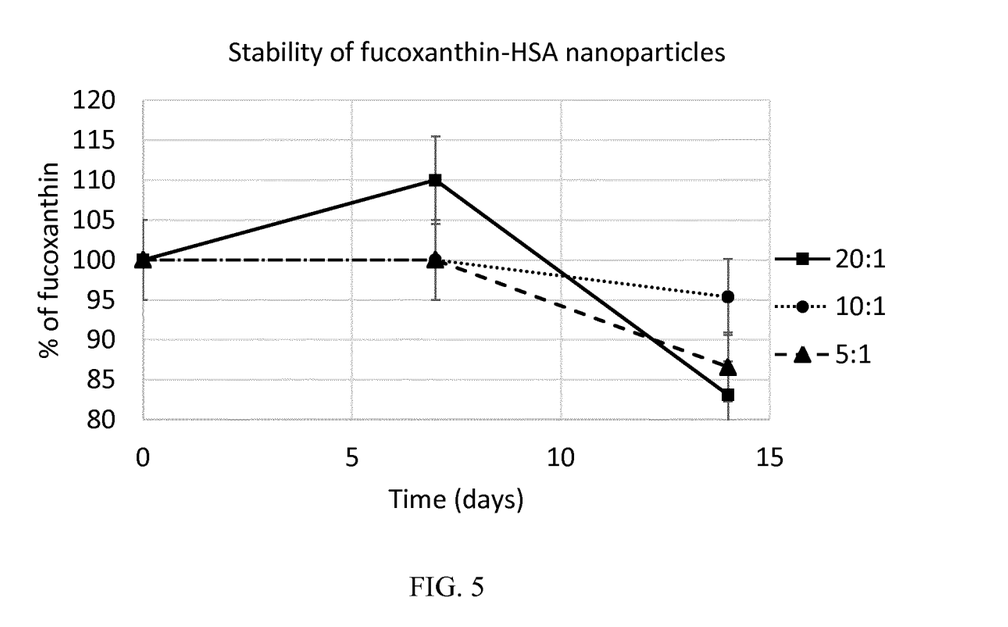
FIG. 5 shows the percentage of fucoxanthin in nanoparticles of human serum albumin (HSA) and fucoxanthin dispersed in aqueous solution after 7 and 14 days from their preparation. Weight ratio albumin/fucoxanthin (■) 20:1; (●) 10:1; (▲) 5:1.
Figure 6:
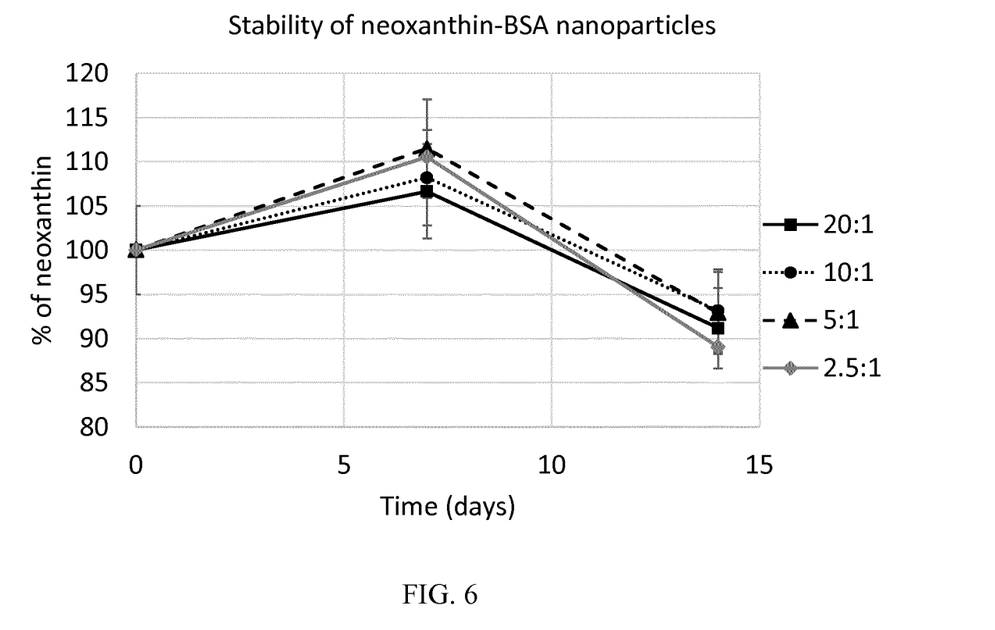
FIG. 6 shows the percentage of neoxanthin in nanoparticles of bovine serum albumin (BSA) and neoxanthin dispersed in aqueous solution after 7 and 14 days from their preparation. Weight ratio albumin/neoxanthin (■) 20:1; (●) 10:1; (▲) 5:1; (◆) 2.5:1.

As can be shown in FIGS. 4-6, no significant degradation of the xanthophyll was detected independently of the ratio of albumin:xanthophyll analyzed or the storage condition after 14 days of preparation.

Example 4

Modulation of Glucocorticoid Receptor

The present study aimed to determine if xantophylls and carotenes act as antagonists of glucocorticoid receptor (GR). The effects of neoxanthin, fucoxanthin, astaxanthin, beta-carotene, isofucoxanthin and lutein were assessed.

An antagonist assay for GR was performed by SelectScreen® Cell-Based Nuclear Receptor Profiling Service of Life Technologies. In this assay, an engineered cell line (UAS-bla HEK 293T) expressing GR is used to test the action of the different xanthophylls. Detection method is based on a beta-lactamase reporter gene (bla) combined with a FRET-enabled substrate. The data obtained in these assays was modelled to a sigmoidal dose response curve.

Firstly, neoxanthin was tested against the agonist dexamethasone. Neoxanthin inhibitory action starts between 0.1 and 0.3 μM and is above 85% at 10 μM. On a second assay, fucoxanthin activity was analyzed. In this case, fucoxanthin acts as an antagonist from a concentration of 30 nM and achieves 50% of inhibition at 10 μM. Similar results were obtained when isofucoxanthin and lutein were analyzed. They both achieve a maximum of 80% GR inhibition when used at 10 μM. However, when astaxanthin and beta-carotene were tested, neither compound exercised an antagonist effect on GR, as they were not capable of significantly inhibiting dexamethasone action.

Figure 7:
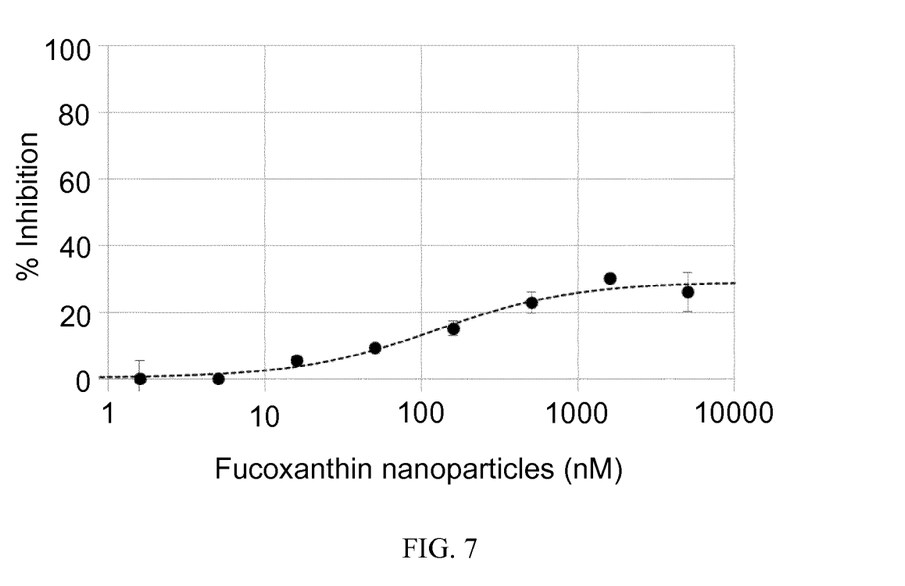
FIG. 7. Dose-response curve of albumin-fucoxanthin nanoparticles antagonism to GR. Dexamethasone was used as a glucocorticoid stimuli. Mifepristone was the control antagonist of the assay (IC50 0.674 nM).

In order to determine whether albumin-xanthophyll nanoparticles retain this anti-GR activity, BSA-fucoxanthin nanoparticles were tested. They were obtained following the method of the present invention, with a weight ratio of albumin/xanthophyll of 20:1. Results, shown in FIG. 7, determine that the nanoparticles act as GR antagonists from a concentration of 30 nM and achieve 30% of inhibition at 10 μM.

In conclusion, only some xanthophylls are able to inhibit or modulate the action of glucocorticoid agonists. Moreover, this activity is retained when they are formulated as albumin nanoparticles. Compounds as neoxanthin, fucoxanthin, isofucoxanthin or lutein possess that characteristic, whereas astaxanthin and beta-carotene do not. Therefore, the antagonist activity is not present in all carotenoids (xanthophylls and carotenes) and it is not an intrinsic characteristic of xanthophylls or carotenes.

Comparative Example 5

Preparation and Characterization of Astaxanthin Nanoparticles

Bovine serum albumin (BSA) as the matrix-forming material and astaxanthin as a xanthophyll were used in this experimental set up. Nanoparticles having the following albumin:xanthophyll weight ratio were prepared: 20:1; 5:1 and 1:1.

To prepare bovine serum albumin (BSA)—astaxanthin nanoparticles, albumin (20 mg, 5 mg or 1 mg depending on the protein:carotenoid ratio) was dissolved in 1 mL deionized water and 1 mg of astaxanthin was dissolved in 0.25 mL THF. The astaxanthin solution was slowly added to the BSA solution under stirring and nitrogen atmosphere. When the addition of carotene was completed the solution was stirred at room temperature for 10 additional minutes. The organic solvent (THF) in the mixed solution was slowly removed by speed vacuum at 25° C. Distillation was completed when the total solution volume was reduced by ⅔. Finally, the nanoparticle solutions were filtered through a 0.22 μm PES membrane filter and immediately stored in the dark at 4° C.

The quantification of astaxanthin incorporated in the nanoparticles was performed by means of a 1100 series HPLC device (Agilent Technologies, Waldbronn, Germany) with a diode array detector (474 nm). Separation was performed on a 100×4.6 mm Kromaphase C18 column (Bischoff, Leonberg, Germany) with an average pore diameter of 100 Å and a particle size of 5 μm at room temperature. The mobile phase composition was acetone (A) and water (B) at a flow rate of 1 mL/min. The elution proceeded isocratically at 65% A for 2.5 min and was followed by a linear gradient to 100% A until minute 8. This percentage of A was maintained for 3 additional minutes. The injection volume was 5 μL.

Sample preparation for HPLC-PDA analysis was performed as following: 50 μL samples of the solution before and after filtration were mixed with 950 μL of acetone and stirred for 30 min on an orbital shaker for 30 min. The solution was then centrifuged at 13000 rpm for 1 min. The supernatant was recovered by decantation and used for HPLC analysis.

Figure 8:
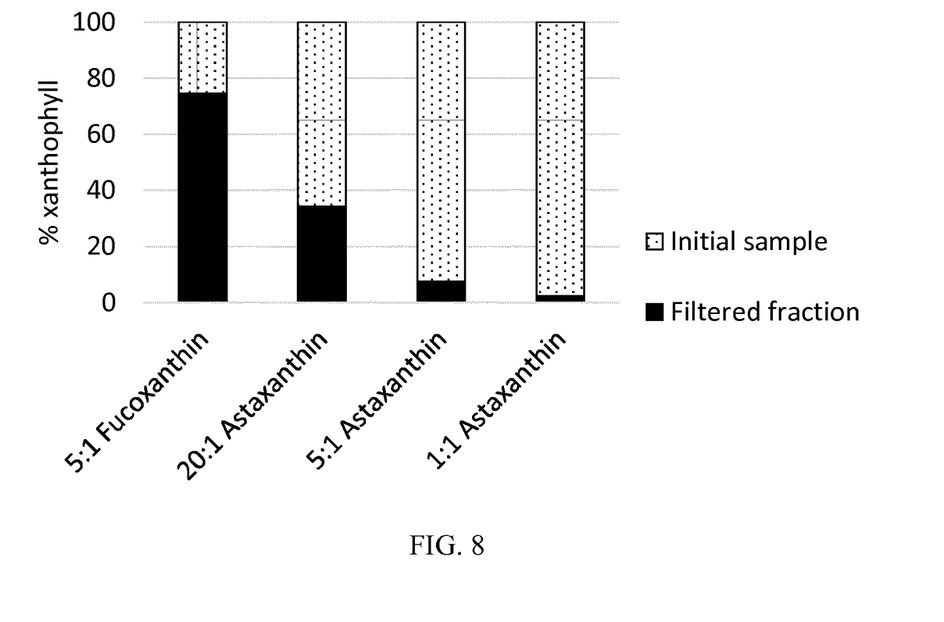
FIG. 8. Percentage of xanthophyll loss in nanoparticle filtration through 0.22 μm PES membrane filter. Nanoparticles of BSA and astaxanthin or fucoxanthin were formed at different weight ratio albumin:xanthophyll and are dispersed in aqueous solution. Initial sample (dotted); filtered fraction (black).

High astaxanthin loss was detected in filtered samples, independently of the ratio of albumin:astaxanthin analyzed. As shown in FIG. 8, from 66% to 98% of astaxanthin was lost in the filtration step. In contrast, when filtering fucoxanthin nanoparticles described in examples 1-3, only 25% of the xanthophyll was in an insoluble nanoparticulated form. This result indicates that a high amount of aggregates (>220 nm) formed during the preparation of astaxanthin nanoparticles.

There was also a significant loss of astaxanthin during the process, as it precipitated in the reaction vessel, due the low solubility of this xanthophyll. Astaxanthin precipitated immediately after addition in the albumin solution, causing the formation of aggregates with poor solubility and hampering the nanoparticle formation. The formation of aggregates with poor solubility was not observed when fucoxanthin was used as xanthophyll. During distillation, sample precipitation was also observed, which was never experienced when the xanthophyll used was fucoxanthin. In this way, the amount of astaxanthin incorporated in soluble nanoparticles was very low.

The invention claimed is:

1. A nanoparticle comprising a solid matrix, said solid matrix comprising albumin and a xanthophyll selected from the group consisting of α-cryptoxanthin, β-cryptoxanthin, adonirubin, adonixanthin, alloxanthin, amarouciaxanthin A, antheraxanthin, auroxanthin, caloxanthin, cantaxanthin, capsanthin, capsanthin-5-6-epoxide, capsorubin, crocoxanthin, diadinoxanthin, diatoxanthin, echinenone, fucoxanthin, fucoxanthinol, -iso-fucoxanthin, iso-fucoxanthinol, lutein, luteoxanthin, mutatoxanthin, neoxanthin, nostoxanthin, violaxanthin, zeaxanthin and combinations or derivatives thereof, wherein the weight ratio of albumin to the xanthophyll ranges from 1:1 to 20:1.

2. The nanoparticle according to claim 1, wherein the albumin is human serum albumin or bovine serum albumin.

3. The nanoparticle according to claim 1, wherein the xanthophyll is selected from amarouciaxanthin A, fucoxanthin, fucoxanthinol, neoxanthin, lutein and combinations thereof.

4. The nanoparticle according to claim 1, wherein the xanthophyll is amarouciaxanthin A.

5. The nanoparticle according to claim 1, wherein the xanthophyll is fucoxanthin or neoxanthin.

6. The nanoparticle according to claim 1, having a mean particle size from 10 to 200 nm.

7. The nanoparticle according to claim 1, wherein the solid matrix is devoid of any coating material.

8. The nanoparticle according to claim 1, wherein the nanoparticle comprises a polymeric coating covering the solid matrix.

9. A method for preparing a nanoparticle as defined in claim 1, said method comprises: a) preparing an aqueous solution of albumin; b) preparing a solution of a xanthophyll or a derivative thereof in an organic solvent; and c) adding the xanthophyll solution to the albumin solution, wherein the content of the organic solvent does not exceed 20% v/v with respect to the total volume of the resulting mixture.

10. The method according to claim 9, which further comprises drying the nanoparticles once they are formed.

11. A composition comprising a plurality of nanoparticles as defined in claim 1.

12. The composition according to claim 11 further comprising a food, pharmaceutical, cosmeceutical or nutraceutical acceptable carrier.

13. The composition according to claim 11, wherein the nanoparticles are in the form of a dry powder.

14. A food, pharmaceutical, cosmeceutical or nutraceutical product comprising a plurality of nanoparticles as defined in claim 1 or a composition comprising a plurality of the nanoparticles.

15. A method for the treatment or prevention of a disease involving the production of reactive oxygen species comprising administering to a subject in need thereof a nanoparticle as defined in claim 1 or a pharmaceutical product comprising a plurality of the nanoparticles.

16. A method for the treatment or prevention of a disease mediated by glucocorticoid receptor activity comprising administering to a subject in need thereof a nanoparticle as defined in claim 1 or a pharmaceutical product comprising a plurality of the nanoparticles.

* * * * *